United States Patent [19]

Gibbs

[11] Patent Number: 5,804,598

[45] Date of Patent: Sep. 8, 1998

[54] XYLOMOLLIN DERIVATIVES FOR USE AS INSECT FEEDING DETERRENTS

[75] Inventor: Don E. Gibbs, Kansas City, Mo.

[73] Assignee: Rockhurst University, Kansas City, Mo.

[21] Appl. No.: 820,840

[22] Filed: Mar. 20, 1997

Related U.S. Application Data

[60] Provisional application No. 60/013,817, Mar. 21, 1996.

[51] Int. Cl.$^6$ ............................. A01N 43/08; A01N 43/16
[52] U.S. Cl. ........................... 514/456; 514/460; 514/470
[58] Field of Search ..................................... 514/456, 460, 514/470

[56] References Cited

U.S. PATENT DOCUMENTS

| | | | |
|---|---|---|---|
| 4,676,985 | 6/1987 | Gould et al. | 424/195.1 |
| 4,855,319 | 8/1989 | Mikolajezak et al. | 514/473 |
| 4,960,791 | 10/1990 | Klocke et al. | 514/468 |
| 5,047,242 | 9/1991 | Klocke et al. | 424/195.1 |
| 5,290,557 | 3/1994 | Mason et al. | 424/410 |

FOREIGN PATENT DOCUMENTS 1590174  5/1981  United Kingdom .

OTHER PUBLICATIONS

Kubo, I., Miura, I. and Nakanishi, K., The Structure of Xylomollin, a Secoiridoid Hemiacetal Acetal, Journal of American Chemical Society, Oct. 13, 1976, pp. 6704–6705.

Yuk–Sun Lam, P. and Frazier, J.L., Model Study on the Mode of Action of Muzigadial Antifeedant, Tetrahedron Letters, vol. 28, No. 45, pp. 5477–5480, 1987, Printed in Great Britain.

*Primary Examiner*—Allen J. Robinson
*Attorney, Agent, or Firm*—Litman, McMahon, & Brown, L.L.C.

[57] ABSTRACT

Synthetic derivatives or intermediates of xylomollin are identified which can be used as insect feeding deterrents. The identified derivatives or intermediates exhibiting anti-feeding activity include glutaraldehyde and carbocyclic or heterocyclic dialdehydes wherein the aldehyde groups are positioned on adjacent carbons of the carbocyclic or heterocyclic rings. The active compounds also include the hemiacetal hemiacetal equivalents, the acetal hemiacetal equivalents and the vinyl ether equivalents of the dialdehydes.

42 Claims, No Drawings

XYLOMOLLIN DERIVATIVES FOR USE AS INSECT FEEDING DETERRENTS

This application is a non-provisional application based on Provisional Application Serial No. 60/013,817 filed Mar. 21, 1996, and entitled INSECT FEEDING DETERRENTS AND THEIR SYNTHESIS.

BACKGROUND OF THE INVENTION

The present invention relates to the identification of compounds which deter feeding by insects and in particular such compounds which are structurally related to xylomollin, a naturally occurring feeding deterrent.

Heavy use of insecticides presents environmental dangers and promotes the development of resistant insect populations. One alternative to present practices relating to insecticide use involves the application on crops of chemicals which inhibit or deter feeding thereon by insects. Use of naturally occurring feeding deterrents and their derivatives for crop protection is appealing because such compounds do not need to be toxic to work and therefore the additional concerns of toxicity to other animals, and in particular to mammals, are avoided. Folklore and stories of traditional farming practices are replete with references to feeding deterrent or repellent properties of plants. A well known practice involves the placement of hedge apples in the corners of basements or root cellars to repel crickets and other insects, spiders and even some rodents.

Extracts from plants known to exhibit antifeeding activity have been used in compositions developed for commercial utilization. For example, U.S. Pat. No. 5,290,557 to Mason et al. discloses the use of saponin containing extracts of *Yucca schidigera* as an antifeedant to control terrestrial mollusks. Similarly, U.S. Pat. No. 4,676,985 to Gould et al. discloses a process of protecting crops from damage by coating seeds or seedlings with an extract from plants having feeding deterrent activity such as extracts from butterfly milkweed, English ivy, santolina, bergamot, clary and swamp milkweed.

Others have focused on identifying derivatives of naturally occurring insect feeding deterrents which also exhibit feeding deterrent activity and which can be synthesized commercially. U.S. Pat. No. 5,047,242 to Klocke et al. identifies derivatives of azadirachtin which exhibit antifeedant activity. Azadirachtin is a naturally occurring feeding deterrent which can be isolated from the seeds of the neem tree and from the fruits of the chinaberry tree. U.S. Pat. No. 4,960,791 to Klocke et al. identifies antifeedant derivatives of salannin which is a naturally occurring insect antifeedant related to azadirachtin. U.S. Pat. No. 4,855,319 to Mikolajczak et al. discloses use of asimicin as a feeding deterrent. Asimicin is a derivative of tetrahydrofuranoid acetogenins, which are characteristic of the Annonaceae plant family and known feeding deterrents.

As of yet, it does not appear that any of these compositions have achieved wide-spread commercial use or success. The lack of commercial success of such compositions may be due to the relative high cost in obtaining large quantities of the specified plant extracts or in synthesizing the relatively complex chemical derivatives of naturally occurring antifeedants identified to date. Derivatives of naturally occurring feeding deterrents still provide a promising avenue for alternatives to currently available insecticides for use in integrated pest management programs. The compounds should be ecologically sound and non-toxic to mammals. The synthesis of these compounds should be relatively inexpensive and result in the production of relatively stable compounds with the minimal structural components necessary for relatively high activity.

Xylomollin, which has the following chemical formula:

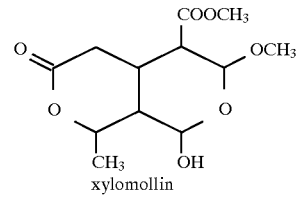

xylomollin is found in the unripened fruit of the East African tree *Xylocarpus molluscensis* (Meliaceae) and has been previously identified as a potent feeding deterrent. However, due to the complexity of xylomollin's chemical structure, currently known methods of synthesizing xylomollin are prohibitively expensive for commercial purposes.

SUMMARY OF THE INVENTION

The present invention includes the identification of synthetic derivatives or intermediates of xylomollin which can be used as feeding deterrents.

The identified derivatives or intermediates exhibiting antifeeding activity include glutaraldehyde and carbocyclic or heterocyclic dialdehydes wherein the aldehyde groups are positioned on adjacent carbons of five or six member ring compounds as represented by the following formulas:

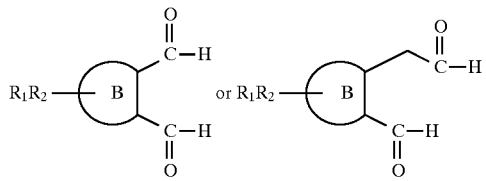

where ring B is a five or six carbon ring or a lactone that may include an alkene function and/or alkyl or hydroxyl groups as substituents. The active compounds also include the acetal hemiacetal equivalents thereof, the hemiacetal hemiacetal equivalents thereof and vinyl ether equivalents thereof.

The acetal hemiacetal and hemiacetal hemiacetal equivalents of the carbocyclic and heterocyclic compounds include:

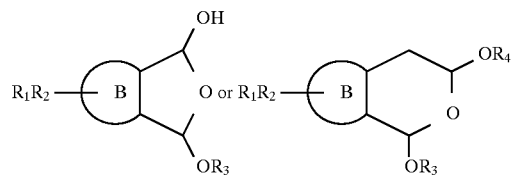

where ring B is a five or six carbon ring or a lactone that may include an alkene function, $R_1$ and $R_2$ comprise H, OH or an alkyl group and $R_3$ and $R_4$ comprise H or an alkyl group. The alkyl groups are preferably $C_1$–$C_5$ alkyl groups, and at least one of $R_3$ and $R_4$ must comprise H.

The vinyl ether equivalents of the carbocyclic and heterocyclic include:

$$R_1R_2 \!-\!\!\!\left(\!\! B \!\!\right)\!\!\!-\! O \text{ or } R_1R_2 \!-\!\!\!\left(\!\! B \!\!\right)\!\!\!-\!\!\!\underset{OR}{\overset{\diagup}{\diagdown}}\!\! O$$

where ring B is a five or six carbon ring or a lactone that may include an alkene function, $R_1$ and $R_2$ comprise H, OH or an alkyl group and $R_3$ comprises H or an alkyl group. The alkyl groups are preferably $C_1$–$C_5$ alkyl groups.

OBJECTS AND ADVANTAGES OF THE INVENTION

The objects of the present invention include: providing feeding deterrent compositions which are relatively non-toxic and relatively inexpensive to manufacture and to apply at concentrations which are effective at deterring feeding on plants and crop material; providing such compositions which are relatively easy to manufacture; providing such compositions which are effective at deterring feeding even at relatively low concentrations with respect to plant or crop material to which the compositions are applied; and providing such compositions which are relatively biodegradable.

It is a further object of this invention to identify the functional groups of naturally occurring xylomollin which account for the feeding deterrent effect of xylomollin and to identify synthetic derivatives which incorporate these functional groups and function as feeding deterrents but are relatively non-toxic and relatively inexpensive to manufacture and to apply at concentrations which are effective at deterring feeding on plants and crop material.

Other objects and advantages of this invention will become apparent from the following description wherein are set forth, by way of illustration and example, certain embodiments of this invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific composition and functional details disclosed herein are not to be interpreted as limiting, but merely as a basis for the claims and as a representative basis for teaching one skilled in the art to variously employ the present invention in virtually any appropriately detailed structure.

The present invention comprises the use of glutaraldehyde and various carbocyclic and heterocyclic dialdehydes and derivatives thereof as feeding deterrents. The carbocyclic and heterocyclic dialdehydes identified for use as feeding deterrents generally include the following:

$$R_1R_2 \!-\!\!\!\left(\!\! B \!\!\right)\!\!\!\overset{\text{C}-\text{H}}{\underset{\text{C}-\text{H}}{\diagup\diagdown}} \text{ or } R_1R_2 \!-\!\!\!\left(\!\! B \!\!\right)\!\!\!\overset{\text{C}-\text{H}}{\underset{\text{C}-\text{H}}{\diagup\diagdown}}$$

where ring B is a five or six carbon ring or a lactone that may include an alkene function and/or alkyl or hydroxyl groups as substituents. The active compounds also include the acetal hemiacetal equivalents thereof, the hemiacetal hemiacetal equivalents thereof and vinyl ether equivalents thereof.

The active compounds also include the acetal hemiacetal, hemiacetal hemiacetal and vinyl ether derivatives of the above noted dialdehydes. The acetal hemiacetal and hemiacetal hemiacetal equivalents of the carbocyclic and heterocyclic compounds include:

$$R_1R_2 \!-\!\!\!\left(\!\! B \!\!\right)\!\!\!-\! O \text{ or } R_1R_2 \!-\!\!\!\left(\!\! B \!\!\right)\!\!\!-\!\!\!\underset{OR_3}{\overset{OR_4}{\diagdown}}\!\! O$$

where ring B is a five or six carbon ring or a lactone that may include an alkene function, $R_1$ and $R_2$ comprise H, OH or an alkyl group and $R_3$ and $R_4$ comprise H or an alkyl group. The alkyl groups are preferably $C_1$–$C_5$ alkyl groups, and at least one of $R_3$ and $R_4$ must comprise H.

The vinyl ether equivalents of the carbocyclic and heterocyclic include:

$$R_1R_2 \!-\!\!\!\left(\!\! B \!\!\right)\!\!\!-\! O \text{ or } R_1R_2 \!-\!\!\!\left(\!\! B \!\!\right)\!\!\!-\!\!\!\underset{OR}{\overset{\diagup}{\diagdown}}\!\! O$$

where ring B is a five or six carbon ring or a lactone that may include an alkene function, $R_1$ and $R_2$ comprise H, OH or an alkyl group and $R_3$ comprises H or an alkyl group. The alkyl groups are preferably $C_1$–$C_5$ alkyl groups.

In the presence of water, the acetal vinyl ether derivative will break down to the acetal hemiacetal derivative, a portion of which then breaks down to the dialdehyde. A portion of the hemiacetal hemiacetal derivative interconverts to and exists in equilibrium with the dialdehyde. Similarly a portion of the acetal hemiacetal derivative will convert to the dialdehyde in an aqueous solution. The vinyl ether derivatives are generally more stable than the acetal hemiacetal derivatives and the hemiacetal hemiacetal derivatives which tend to be more stable than the dialdehyde equivalents. Therefore the preferred compounds for use would generally comprise the vinyl ether derivatives, the acetal hemiacetal derivatives and the hemiacetal hemiacetal derivatives which are then converted to the dialdehyde in the application environment through the reaction with water present therein.

It has been postulated that an insect food sensory protein has amino and thiol groups with rigid steric requirements for binding via conjugate addition/redox reaction or imine/heterocycle formation with active compounds. It has been further postulated that the aldehyde functional groups on the xylomollin dialdehyde derivative bind with the insect food sensory protein to deter feeding generally as follows:

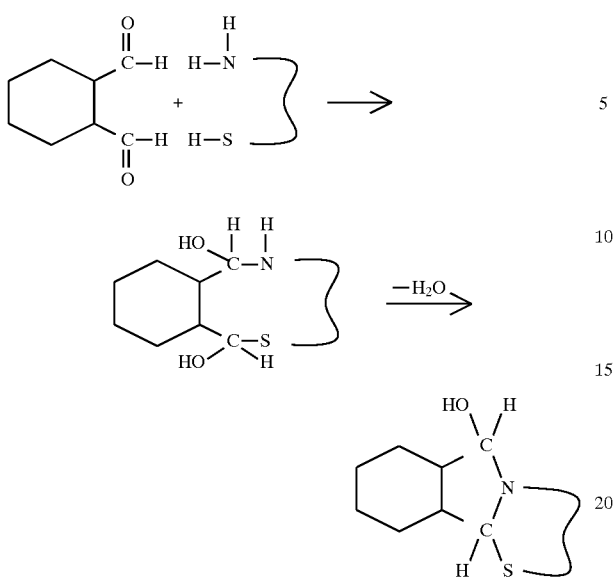

It is not exactly known how this reaction deters feeding. The reaction is believed to effect the insect nervous system and interfere with the insects ability to process information concerning food possibly suppressing hunger or decreasing the palatability of the treated food. The active compounds may also arrest insect development beyond the larval stage.

The following compounds have been tested and have shown feeding deterrent effect:

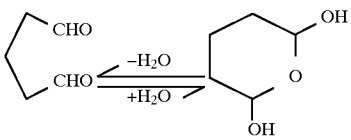 1

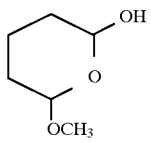 2

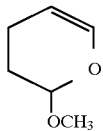 3

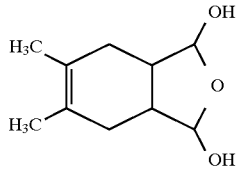 4

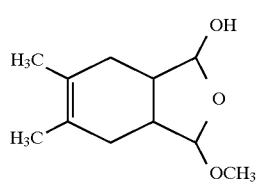 5

The results of the testing are reported below with reference to the corresponding reference numerals noted above.

In addition to the above noted compounds, preferred active compounds for feeding deterrent effect generally include the following along with isomers thereof:

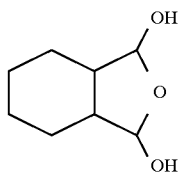 6

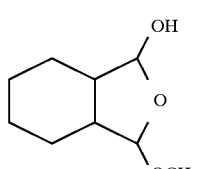 7

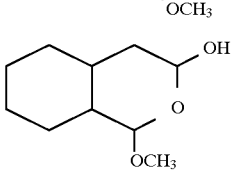 8

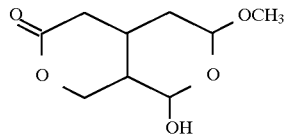 9 compounds and their corresponding dialdehydes and vinyl ethers.

Glutaraldehyde (compound 1 above) free of polymerization products was prepared by saturating 25 ml of a 25% aqueous solution of glutaraldehyde with sodium chloride and extracting the mixture with three 50 ml portions of dichloromehtane. The combined extracts were dried with sodium sulfate and the solvent was removed on a rotary evaporator under water aspirator vacuum using a water bath at 30 degrees Centigrade. The pure sample of glutaraldehyde thus obtained was used within 3 days for bioassays.

To produce compound 2, a solution of 1.14 g or 10 mmol 2-methoxy-3,4 dihydropyran (compound 3 which is commercially available) and 0.18 g or 10 mmol of water in 20 ml of acetonitrile was stirred with 2.0 g of Amberlyst-15 (H$^+$) resin for 4 hours. The resin was removed by filtration and the solvent was removed by rotary evaporation to give a colorless liquid that was 90–92% compound 2 and 4–6% glutaraldehyde (compound 1) according to NMR spectroscopy. To produce compound 4, a mixture of 2,3-dimethyl-1,3-butadiene (0.328 g, 4 mmol), 2,5-demethoxy-2,5-dihydrofuran (0.520 g, 4 mmol), 0.25 ml of water and 50 mg of hydroquinone in a sealed vial was heated in an oil bath at 70 degrees Fahrenheit for 12 hours. The resulting mixture consisted of two liquid phases, the lower of which contained 90% of compound 4.

To produce compound 5, the procedure describe above for compound 4 was used except that the volume of water was 0.070 ml. A homogeneous mixture was formed consisting of 90% of compound 5 plus 3–4% of compound 4, 3–4% of the corresponding cyclic dimethyl acetal and 2–4% of starting material.

Compounds 6 and 7 can be produced using the same procedure as described above for compounds 4 and 5 but using 1,3 butadiene instead of 2,3-dimethyl-1,3-butadiene as the starting material.

Although the carrier utilized in the tests discussed below comprises an organic solvent, ethyl acetate, it is not intended that the present application be limited to any particular carrier and it is foreseen that the active compounds of the present invention could be applied utilizing a wide range of carriers or formulations now known or subsequently developed. It is foreseen that the active compounds could be applied to crop or plant material in liquid or solid compositions or in solid suspensions or without a carrier. Possible carriers include water or vegetable oil. It is also foreseen that a wide range of additives could also be utilized in the feeding deterrent compositions to facilitate application, to stabilize the composition and for other reasons well known in the art.

The feeding deterrent effect of the active compounds was evaluated through choice tests and weight gain tests on third to fifth instar larvae of Tenebrio molitor (mealworm, flour beetle larvae), third-instar larvae of Manduca sexta (tomato hornworm) and with juvenile Acheta domestica (common cricket). Screening for toxicity was done with larvae of Artemia salina (brine shrimp). Insect cultures and food were obtained from Carolina Biological Supply Co., Burlington, N.C.

Test compounds in an ethyl acetate solution were applied by pipet to a weighed food sample and the mixture was stirred thoroughly in glass or stainless steel trays. References to concentrations of test compounds are reported as parts per million (ppm) by weight of pure test compound relative to the weight of the food sample. Treated food was left in open trays for twenty-four hours before insects were introduced. Controls of food treated with ethyl acetate were prepared according to the same procedure. Insect trials with food treated by solvent only (control) versus food with no treatment showed no evidence of solvent residue effects.

For the choice tests, forty T. molitor larvae were placed on a tray having a first and a second supply of bran meal (60 grams each) on opposite ends thereof. The larvae were placed in groups on each food supply. The first supply of bran meal was treated with a solution of the test compound and the carrier, ethyl acetate as noted above. The test compound was applied to the food at a selected concentration (generally 400, 800 or 1000 parts per million, i.e. weight of test compound to weight of bran meal). The second supply of bran meal was treated with an equivalent amount of ethyl acetate as noted above. The second supply of food may be referred to as untreated food. The first and second supplies of bran meal were maintained in separate areas in the container separated by a screen across which the larvae could traverse. The trays were covered with lids that allowed air flow.

The number of larvae at each end were counted at 7-day intervals. The percentage of larvae on the control or untreated food is indicative of the feeding deterrent effect of the test compound.

Growth tests of T. molitor were done by putting 40 larvae on 120 grams of treated and untreated food and periodically weighing the insects. Weight gain for insects on treated food is reported as a percentage of the weight gain for insects on the control or untreated food (i.e. weight gain on treated/weight gain on control). The percentage of dead insects was also recorded. Typical mortality for the controls were 0% at 7 days, 3% at 14 days and 5% at 21 days.

Feeding tests with M. sexta were made by putting one insect in a covered dish containing two 3.5 cm culture dishes. The food was prepared according to the formula of Yamamoto reported in Yamamoto, R. T., J. Econ. Entom. 1969, 62, 1427. One dish contained 5.0 grams of food treated with the test compound and solvent and the other contained 5.0 grams of food treated with solvent only. Each dish was weighed at 1-day intervals for one week.

Feeding tests were also conducted with azadirachtin, the principle active component of neem oil, a natural product with well-documented insect feeding deterrence. Azadirachtin was obtained from Sigma Chemical Co., St. Louis, Mo. Results of feeding tests are shown in Table 2.

Table 1 provides results from the choice tests with T. molitor. The table includes an indication of the percentage of insect larvae in the area of the untreated food (i.e. the percentage which preferred the untreated food). The reference to days with each percentage indicates the number of days from the beginning of the test on which the observation was made.

TABLE 1

Choice Tests for Glutaraldehyde and its Derivatives

| Test Compound | Insect | Conc. (ppm) | % Insects on untreated food | |
|---|---|---|---|---|
| | | | (7 days) | (14 days) |
| (1) glutaraldehyde | T. molitor | 1000 | 55 | 48 |
| (2) | T. molitor | 1000 | 72 | 56 |
| (3) | T. molitor | 1000 | 52 | 54 |

TABLE 2

Weight Change Relative to Control

| Test Compound | Insect | Conc. (ppm) | % Wt change v. control | |
|---|---|---|---|---|
| | | | (7 days) | (14 days) |
| (1) glutaraldehyde | T. molitor | 1000 | 11 | 45 |
| (2) | T. molitor | 1000 | 16 | 32 |
| (3) | T. molitor | 1000 | 13 | 30 |

TABLE 3

Feeding Rate Relative to Control

| Test Comppound | Insect | Conc. (ppm) | % Wt change of treated control (7 days) |
|---|---|---|---|
| (5) | M sexta | 400 | 5 |
| azadirachtin | M sexta | 50 | 100 |

TABLE 4

Mortality Relative to Control

| Test Compound | Insect | Conc. (ppm) | % Mortality v. control | |
|---|---|---|---|---|
| | | | (7 days) | (14 days) |
| (1) glutaraldehyde | T. molitor | 1000 | 0 | 3 |
| (2) | T. molitor | 1000 | 3 | 10 |
| (3) | T. molitor | 1000 | 3 | 5 |
| (4) | T. molitor | 800 | 93 | 20* |
| (5) | T. molitor | 400 | 40 | 92 |
| azadirachtin | T. molitor | 2 | 10 | 50 |

*The 20% mortality rate represents the mortality rate on the 14th day after treatment of the food and in which the insects were introduced to the food seven days after treatment of the food as opposed to 24 hours for the other assays and for a new group of insects.

Although test compounds 1–3 only appear to show a slight feeding deterrent effect with respect to the choice test, the feeding deterrent effect of these compounds with respect to the weight change tests is significant. Similarly results of the test comparing the weight change of the food treated with test compound 5 versus food treated with a control and fed upon by M. sexta showed significant feeding deterrent effect particularly when compared to the results of a similar test with Azadirachtin. Although the mortality rate of insects which fed upon food treated with test compounds 4 and 5 appeared relatively high, it is unclear as to whether the test compounds 4 and 5 are toxic at the dosages utilized or whether the feeding deterrent effect resulted in the high mortality rate. For example, the compounds may prevent the insect from feeding or prevent the insect from developing properly which may result in death.

Tests done on an acetal acetal equivalent of test compounds 4 and 5 indicated no feeding deterrent effect. Additional research is necessary to reach any conclusions as to whether the acetal acetal equivalents of any of the above described compounds will exhibit feeding deterrent or antifeedant activity effect. In addition, it is foreseeable that the acetal acetal equivalents might be applicable for feeding deterrent effect in that they may gradually break down to the active equivalents so as to be usable in a time released type application.

Although the active compounds disclosed herein are discussed for use in deterring insects from feeding of plant and crop material and the like it is foreseen that the active compounds may also exhibit a feeding deterrent effect on terrestrial mollusks, nematodes or other related creatures which feed on plant and crop material.

Further it is foreseen that various chemical equivalents or isomers of the specified active compounds may also provide a feeding deterrent effect.

It is to be understood that while certain forms of the present invention have been illustrated and described herein, it is not to be limited to the specific forms or compositions, equivalents or isomers described and shown.

What is claimed and desired to be secured by letters patent is as follows:

1. An insect antifeedant composition comprising:
   an insect antifeedant effective amount of an active compound of the formula:

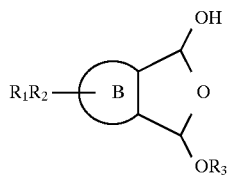

wherein ring B is a 5 or 6 carbon ring, or a lactone, that may include an alkene function and $R_1$ is H, OH or an alkyl, $R_2$ is H, OH or an alkyl and $R_3$ is H or an alkyl, and a carrier.

2. The insect antifeedant composition as in claim 1 comprising an antifeedant effective amount of the dialdehyde equivalent of said active compound.

3. The insect antifeedant composition as in claim 1 comprising an antifeedant effective amount of the vinyl ether equivalent of said active compound.

4. The insect antifeedant composition as in claim 1 wherein said active compound comprises:

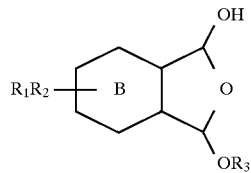

wherein ring B may include an alkene function and $R_1$ is H, OH or $C_1$–$C_5$ alkyl, $R_2$ is H, OH or $C_1$–$C_5$ alkyl and $R_3$ is H or a $C_1$–$C_5$ alkyl.

5. The insect antifeedant composition as in claim 4 comprising an antifeedant effective amount of the dialdehyde equivalent of said active compound.

6. The insect antifeedant composition as in claim 4 comprising an antifeedant effective amount of the vinyl ether equivalent of said active compound.

7. The insect antifeedant composition as in claim 1 wherein said active compound comprises:

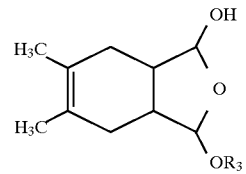

wherein $R_3$ is H or a $C_1$–$C_5$ alkyl.

8. The insect antifeedant composition as in claim 7 comprising an antifeedant effective amount of the dialdehyde equivalent of said active compound.

9. The insect antifeedant composition as in claim 7 comprising an antifeedant effective amount of the vinyl ether equivalent of said active compound.

10. The insect antifeedant composition as in claim 1 wherein said active compound comprises:

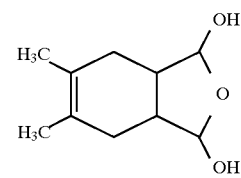

11. The insect antifeedant composition as in claim 9 comprising an antifeedant effective amount of the dialdehyde equivalent of said active compound.

12. The insect antifeedant composition as in claim 9 comprising an antifeedant effective amount of the vinyl ether equivalent of said active compound.

13. The insect antifeedant composition as in claim 1 wherein said active compound comprises:

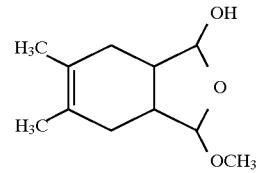

14. The insect antifeedant composition as in claim 13 comprising an antifeedant effective amount of the dialdehyde equivalent of said active compound.

15. The insect antifeedant composition as in claim 13 comprising an antifeedant effective amount of the vinyl ether equivalent of said active compound.

16. The insect antifeedant composition as in claim 1 wherein said active compound comprises:

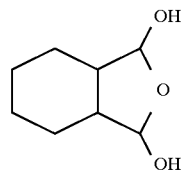

17. The insect antifeedant composition as in claim 16 comprising an antifeedant effective amount of the dialdehyde equivalent of said active compound.

18. The insect antifeedant composition as in claim 16 comprising an antifeedant effective amount of the vinyl ether equivalent of said active compound.

19. The insect antifeedant composition as in claim 1 wherein said active compound comprises:

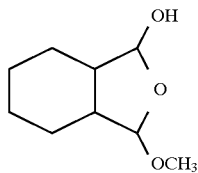

20. The insect antifeedant composition as in claim 19 comprising an antifeedant effective amount of the dialdehyde equivalent of said active compound.

21. The insect antifeedant composition as in claim 19 comprising an antifeedant effective amount of the vinyl ether equivalent of said active compound.

22. An insect antifeedant composition comprising:
an insect antifeedant effective amount of a compound of the formula:

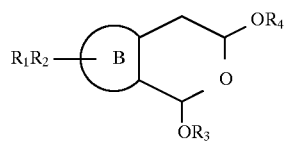

wherein ring B is a 5 or 6 carbon ring, or a lactone, that may include an alkene function and $R_1$ is H, OH or an alkyl, $R_2$ is H, OH or an alkyl, $R_3$ is H or an alkyl and $R_4$ is H or an alkyl, and at least one of $R_3$ and $R_4$ must be H, and a carrier.

23. The insect antifeedant composition as in claim 22 comprising an antifeedant effective amount of the dialdehyde equivalent of said active compound.

24. The insect antifeedant composition as in claim 22 comprising an antifeedant effective amount of the vinyl ether equivalent of said active compound.

25. The insect antifeedant composition as in claim 22 wherein said active compound comprises:

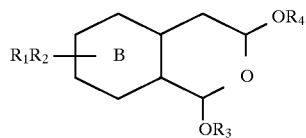

wherein ring B may include an alkene function and $R_1$ is H, OH or $C_1$–$C_5$ alkyl, $R_2$ is H, OH or $C_1$–$C_5$ alkyl, $R_3$ is H or a $C_1$–$C_5$ alkyl and $R_4$ is H or a $C_1$–$C_5$ alkyl, and at least one of $R_3$ and $R_4$ must be H.

26. The insect antifeedant composition as in claim 25 comprising an antifeedant effective amount of the dialdehyde equivalent of said active compound.

27. The insect antifeedant composition as in claim 25 comprising an antifeedant effective amount of the vinyl ether equivalent of said active compound.

28. The insect antifeedant composition as in claim 25 wherein $R_1$ is H, OH or $CH_3$, $R_2$ is H, OH or $CH_3$, $R_3$ is H or $CH_3$ and $R_4$ is H or $CH_3$, and at least one of $R_3$ and $R_4$ must be H.

29. The insect antifeedant composition as in claim 28 comprising an antifeedant effective amount of the dialdehyde equivalent of said active compound.

30. The insect antifeedant composition as in claim 28 comprising an antifeedant effective amount of the vinyl ether equivalent of said active compound.

31. The insect antifeedant composition as in claim 22 wherein said active compound comprises:

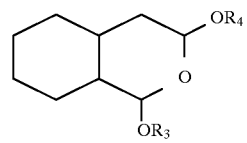

$R_3$ is H or a $C_1$–$C_5$ alkyl and $R_4$ is H or a $C_1$–$C_5$ alkyl, and at least one of $R_3$ and $R_4$ must be H.

32. The insect antifeedant composition as in claim 31 comprising an antifeedant effective amount of the dialdehyde equivalent of said active compound.

33. The insect antifeedant composition as in claim 31 comprising an antifeedant effective amount of the vinyl ether equivalent of said active compound.

34. The insect antifeedant composition as in claim 31 wherein $R_3$ is H or $CH_3$ and $R_4$ is H or $CH_3$, and at least one of $R_3$ and $R_4$ must be H.

35. The insect antifeedant composition as in claim 34 comprising an antifeedant effective amount of the dialdehyde equivalent of said active compound.

36. The insect antifeedant composition as in claim 34 comprising an antifeedant effective amount of the vinyl ether equivalent of said active compound.

37. An insect antifeedant composition comprising:
an insect antifeedant effective amount of a compound of the formula:

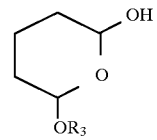

wherein $R_1$ is H or an alkyl, and a carrier.

38. The insect antifeedant composition as in claim 37 comprising an antifeedant effective amount of the dialdehyde equivalent of said active compound.

39. The insect antifeedant composition as in claim 37 comprising an antifeedant effective amount of the vinyl ether equivalent of said active compound.

40. The insect antifeedant composition as in claim 37 wherein $R_1$ is H or $CH_3$.

41. The insect antifeedant composition as in claim 40 comprising an antifeedant effective amount of the dialdehyde equivalent of said active compound.

42. The insect antifeedant composition as in claim 40 comprising an antifeedant effective amount of the vinyl ether equivalent of said active compound.

* * * * *